United States Patent [19]
Adamczyk et al.

[11] Patent Number: 5,464,767
[45] Date of Patent: Nov. 7, 1995

[54] REAGENTS AND METHODS FOR THE QUANTIFICATION OF TOTAL DOXEPINS IN BIOLOGICAL FLUIDS

[75] Inventors: Maciej Adamczyk, Gurnee; Jeffrey R. Fishpaugh, Chicago; Donald Johnson, Lindenhurst; Robert E. Hruska, Libertyville, all of Ill.

[73] Assignee: Abbott Laboratories, Abbott Park, Ill.

[21] Appl. No.: 226,809

[22] Filed: Apr. 12, 1994

Related U.S. Application Data

[60] Division of Ser. No. 916,066, Jul. 24, 1992, Pat. No. 5,332,661, which is a continuation-in-part of Ser. No. 738,400, Jul. 31, 1991, abandoned.

[51] Int. Cl.$^6$ ............................ C12N 9/96; C07K 14/76; C07D 267/16; C07D 311/80
[52] U.S. Cl. .................. 435/188; 530/404; 530/405; 530/406; 540/550; 544/212; 549/223
[58] Field of Search ..................... 435/188; 530/389.8, 530/403, 404, 405, 406; 549/223; 544/212

[56] References Cited

U.S. PATENT DOCUMENTS

| | | | |
|---|---|---|---|
| 4,223,013 | 9/1980 | Hu et al. | 424/177 |
| 4,420,568 | 12/1983 | Wang et al. | 436/536 |
| 4,629,691 | 12/1986 | Collins et al. | 435/188 |
| 5,256,409 | 10/1993 | Blincko | 530/395 |

FOREIGN PATENT DOCUMENTS 0226730  1/1987  European Pat. Off. .

OTHER PUBLICATIONS

M. T. Rosseel, et al, "Quantitative GLC Determination of CIS– and Trans–Isomers of Doxepin and Desmethyldoxepin", J. Pharmaceutical Sciences, vol. 67, pp. 802–805 (1988).
R. Virtanen, et al, "Radioimmunoassay For Doxepin and Desmethyldoxepin", Acta pharmacol., et toxicol., vol. 47, pp. 274–278 (1980).
K. K. Midha, et al, "Radioimmunoassay For Total Doxepin And N–Desmethyl Doxepin In Plasma", Communications in Psychopharmacology, vol., 4, pp. 11–15 (1980).
Y. H. Park, et al, "Quantitative Determination of Doxepin and Nordoxepin in Urine By High–Performance Liquid Chromatography", Journal of Chromatography, vol., 375, pp. 202–206 (1986).
M. N. Al–Bassam, et al, "Nortriptyline Enzyme–Immunoassay" Proc. Int. Symp., Walter de Gruyter & Co., Berlin/New York (Ed.), pp. 375–386 (1978).
I. Lavastre, et al, "The Synthesis Of Metallocene–Labelled Drugs For Biological Assays", Applied Organometallic Chemistry, vol., 4, pp. 9–17 (1990).

Primary Examiner—Mary E. Ceperley

[57] ABSTRACT

Immunoassay methods and reagents for the quantification of total doxepins (i.e., E-doxepin, Z-doxepin, E-desmethyldoxepin, and Z-desmethyldoxepin) in a test sample are disclosed. The quantification of total doxepins is accomplished in an immunoassay employing antibodies and labeled reagents prepared with doxepin derivatives of the Formula II:

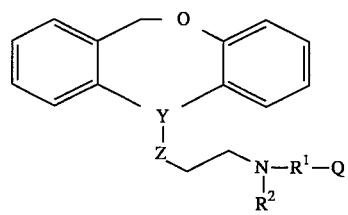

wherein Y-Z can be C=CH or N-CH$_2$, R$_1$ is a linking group, R$_2$ can be H or CH$_3$, and Q can be a detectable moiety or an immunogenic carrier material. The antibody reagent comprises antibodies which are capable of binding to total doxepins and which are produced with one or more immunogens prepared from the doxepin derivative of Formula II, and the labeled reagent is also prepared from the doxepin derivative of Formula II.

19 Claims, 7 Drawing Sheets

6-Carboxyfluorescein active ester

Fn = 6-fluoresceinyl =

Aminomethylfluorescein HCl salt =

AMF =

REAGENTS AND METHODS FOR THE QUANTIFICATION OF TOTAL DOXEPINS IN BIOLOGICAL FLUIDS

This is a divisional of U.S. Ser. No. 07/916,066, filed on Jul. 24, 1992, now U.S. Pat. No. 5,332,661, which is a continuation-in-part of U.S. Ser. No. 07/738,400, filed Jul. 31, 1991, abandoned.

FIELD OF THE INVENTION

The present invention relates to the immunoassay determination of doxepins in a test sample. In particular, the present invention relates to immunogens, antibodies prepared from such immunogens, and labeled reagents for the quantification of total doxepins in a test sample, preferably for use in a fluorescence polarization immunoassay.

BACKGROUND OF THE INVENTION

The monitoring of therapeutic drug levels in biological fluids such as serum, plasma, whole blood, urine, and the like, has become very useful to provide physicians with information to aid in patient management. The monitoring of such drug levels enables adjustment of patient dosage to achieve optimal therapeutic effects, and helps avoid either subthera, peutic or toxic levels. Doxepin is a tricyclic antidepressant drug which exists in two isomeric forms, E-doxepin (Formula IA, R=CH$_3$) and Z-doxepin (Formula IB, R=CH$_3$):

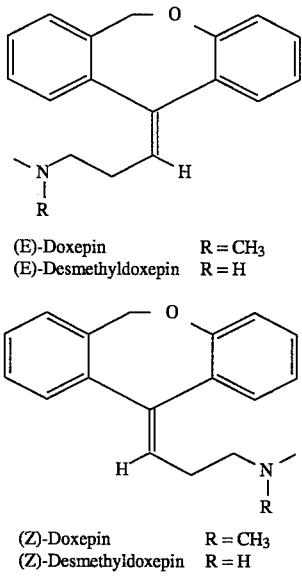

(E)-Doxepin R = CH$_3$
(E)-Desmethyldoxepin R = H (Z)-Doxepin R = CH$_3$
(Z)-Desmethyldoxepin R = H Although doxepin has been found to be very effective in treating chronic depression, its concentration in a patient's blood must be maintained in a therapeutic range. A wide interpatient variation normally exists in human plasma for a given dose. However, high doses have been associated with central nervous system disorders, toxicity, hypertension, seizures, coma and death. Since individuals vary greatly in their response to doxepin, it is necessary to monitor the therapy by measuring the level thereof in, for example, the serum or plasma of the patient.

Doxepin is administered as a mixture of the E-doxepin and Z-doxepin isomers, also referred to as trans-doxepin and cis-doxepin, respectively, at a ratio of about 85:15 (E:Z). Once administered, doxepin is metabolized by N-demethylation to form desmethyldoxepin, which is also active-and which also occurs as both the E and Z isomers thereof (Formulae IA and IB, R=H). For des-methyldoxepin, varying ratios of the isomers have been reported in individual patients.

Since both doxepin (E-isomer and Z-isomer) and desmethyl-doxepin (E-isomer and Z-isomer) are active for treating depressive symptoms, conventional diagnostic techniques for the determination of doxepin levels is based on the measurement of the levels of the respective isomers of doxepin and desmethyldoxepin wherein the therapeutic range ascribed to blood levels in a patient is the total of doxepins and desmethyidoxepins, i.e. E-doxepin plus Z-doxepin plus E-desmethyldoxepin plus Z-desmethyldoxepin equals total doxepins. Concentrations below the range are proposed to be subtherapeutic for the treatment of depression, while levels higher than the range can be associated with undesirable effects including cardiovascular complications, anticholinergic effects, and sedation, without any increase in antidepressant efficacy.

Although the levels of doxepins and desmethyldoxepins can be measured by chromatographic techniques, such as high pressure liquid chromatography [Park, *J. of Chromatogr.*, 375, 202–206 (1986)] or gas chromatography [Rosseel et al., *J. Pharm. Sci.*, 67, 802–805 (1978)], such techniques are labor intensive, requiring highly skilled personnel to perform various cumbersome steps which are time consuming and tedious. Similarly, derivatives of the tricyclic: antidepressant drug known as amitriptyline have been employed for the generation of antisera and labeled reagents for use in a radioimmunoassay system for determining doxepin and desmethyldoxepin levels [Midha and Charette, *Communications In Psychopharmacol.*, 4, 11–15 (1980); Virtanen, et al., *Acta. Pharmacol. Et. Toxicol.*, 47, 274–278 (1980)]. However, such techniques employing non-isomeric immunogens (i.e., linking an N-substituted amitriptyline to a protein carrier) and non-isomeric labeled reagents have failed to demonstrate equivalent recognition of the isomers of doxepin and desmethyldoxepin. In particular, a non-specific fluorescence polarization immunoassay (FPIA) for the detection of the total amount of the four major tricyclic antidepressant drugs is commercially available and described in European Patent. Application Publication No. 226,730 and U.S. Pat. No. 4,420,568 wherein the concentration determined by this assay is only a crude estimation of the total amount of tricyclic antidepressant in plasma or serum. Accordingly, such assay cannot be used to accurately quantify the total amount of all four isomers of doxepin and desmethyldoxepin.

SUMMARY OF THE INVENTION

According to the present invention, the quantification of total doxepins (i.e., E-doxepin, Z-doxepin, E-desmethyidoxepin, and Z-desmethyldoxepin) in a test sample is accomplished in a single immunoassay employing antibodies and labeled reagents prepared with doxepin derivatives of the formula (II):

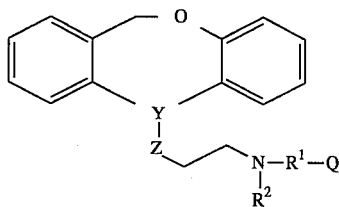

wherein Y-Z can be C=CH or N-CH$_2$, R$_1$ is a linking group comprising from 1 to 6 carbon atoms and 0 to 2 heteroatoms, R$_2$ can be H or CH$_3$, and Q can be a detectable moiety or an immunogenic carrier material. As would be understood by one skilled in the art, when Y-Z is C=CH, such derivative comprises the E-isomer, the Z-isomer, or a mixture of the E-isomer and the Z-isomer thereof.

It is to be understood that a test sample may not necessarily simultaneously contain each one of the E and Z isomers of doxepin and the E and Z isomers of desmethyldoxepin, but that they may be present individually, or in any combination or ratio thereof. Accordingly, the term "total doxepins" and quantification thereof as used herein is intended to include the quantification of any one, combination, or ratio of doxepins and desmethyldoxepins in a test sample.

In particular the immunoassay quantification of total doxepins according to the present invention is accomplished by first contacting the test sample, with a labeled reagent and an antibody reagent, either simultaneously or sequentially in either order. The antibody reagent comprises antibodies which are capable of binding to or recognizing total doxepins wherein the antibodies are produced with one or more immunogens prepared from the doxepin derivative of Formula II where Y-Z can be N-CH$_2$ or C=CH, R$_1$ is a linking group comprising from 1 to 6 carbon atoms and 0 to 2 heteroatoms, R$_2$ can be H or CH$_3$, and Q is an immunogenic carrier material. The labeled reagent is prepared from the doxepin derivative of Formula II where Y-Z is C=CH, R$_1$ is a linking group comprising from 1 to 6 carbon and 0 to 2 heteroatoms, R$_2$ can be H or CH$_3$, and Q is a detectable moiety. The amount of the labeled reagent which either has or has not participated in a binding reaction with the antibodies is then measured as a function of total doxepins in the test sample.

It is to be understood that where Y-Z in the one or more immunogens is N-CH$_2$, and Y-Z in the labeled reagent is C=CH, then the antibodies are produced from a single immunogen and are capable of binding to total doxepins, and the labeled reagent comprises a mixture of the E-isomer and the Z-isomer of the doxepin derivative. Similarly, where Y-Z in the one or more immunogens is C=CH, then the antibody reagent comprises a mixture of antibodies produced from the E-isomer and the Z-isomer of the doxepin derivative, and the labeled reagent comprises a mixture of the E-isomer and the Z-isomer of the doxepin derivative.

DESCRIPTION OF THE INVENTION

Figure 1:
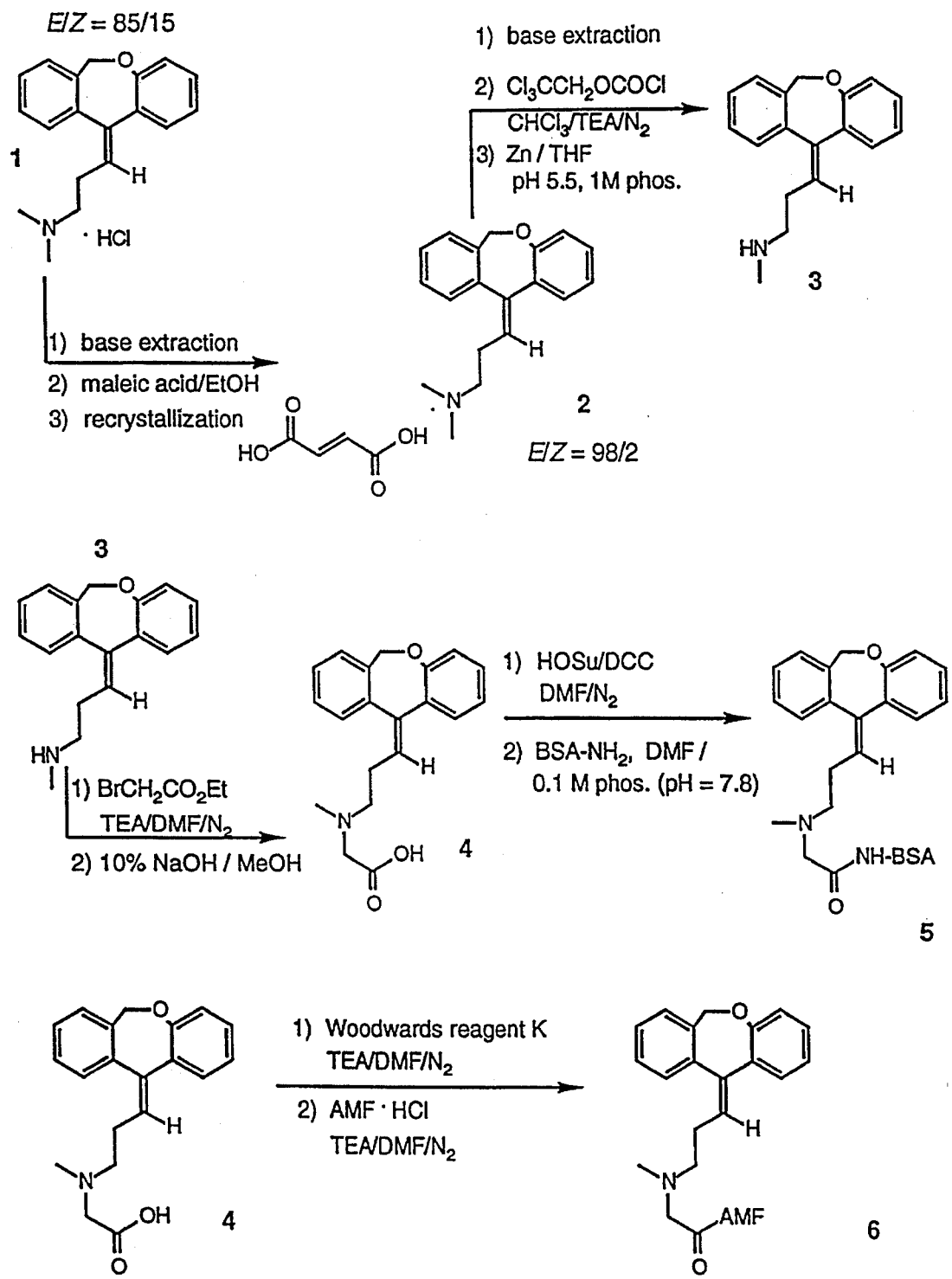
FIG. 1 illustrates the synthetic pathway for the preparation of an immunogen and a fluorescent labeled reagent derived from (E)-doxepin of the present invention.
Figure 2:
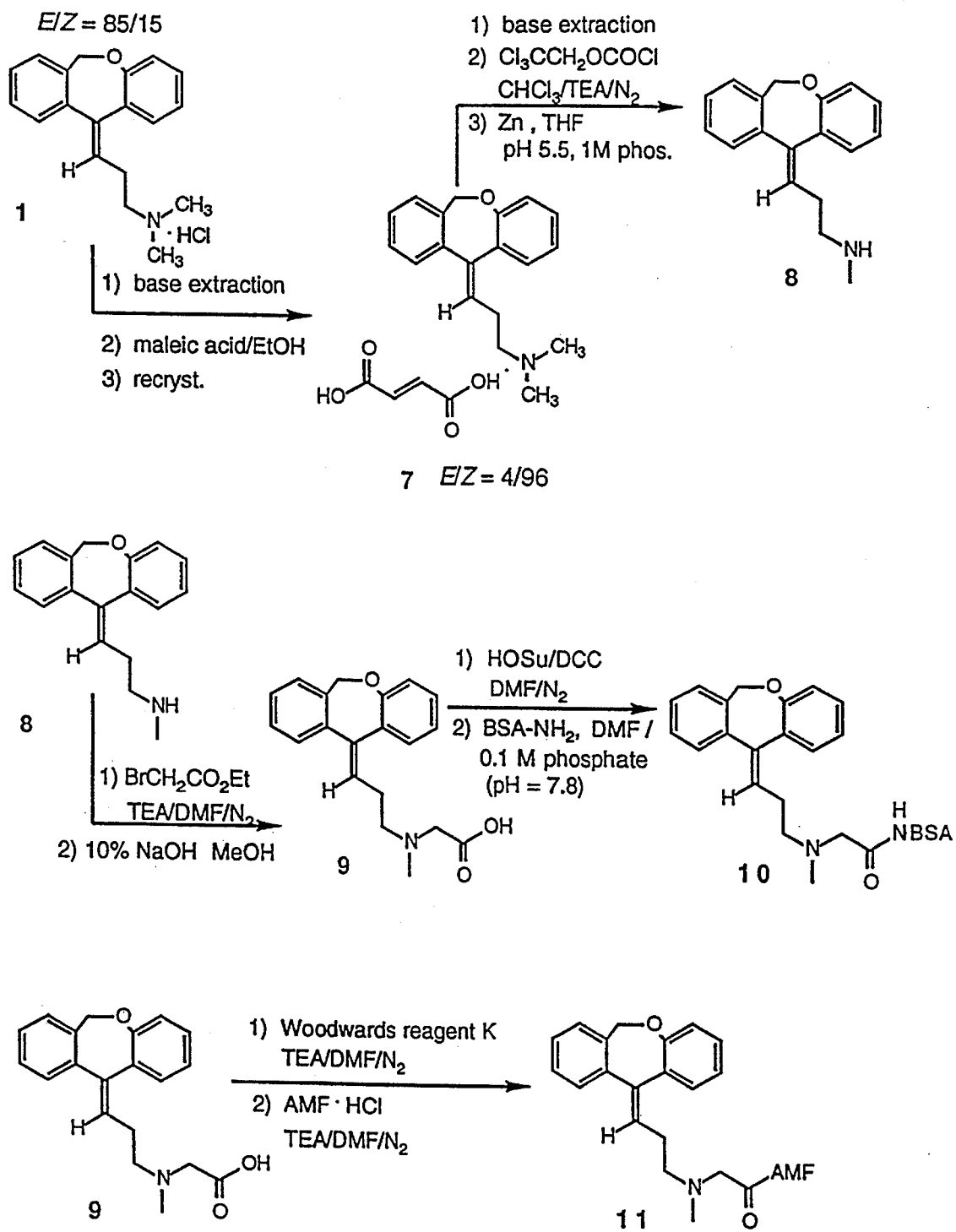
FIG. 2 illustrates the synthetic pathway for the preparation of an immunogen and a fluorescent labeled reagent derived from (Z)-doxepin of the present invention.
Figure 3:
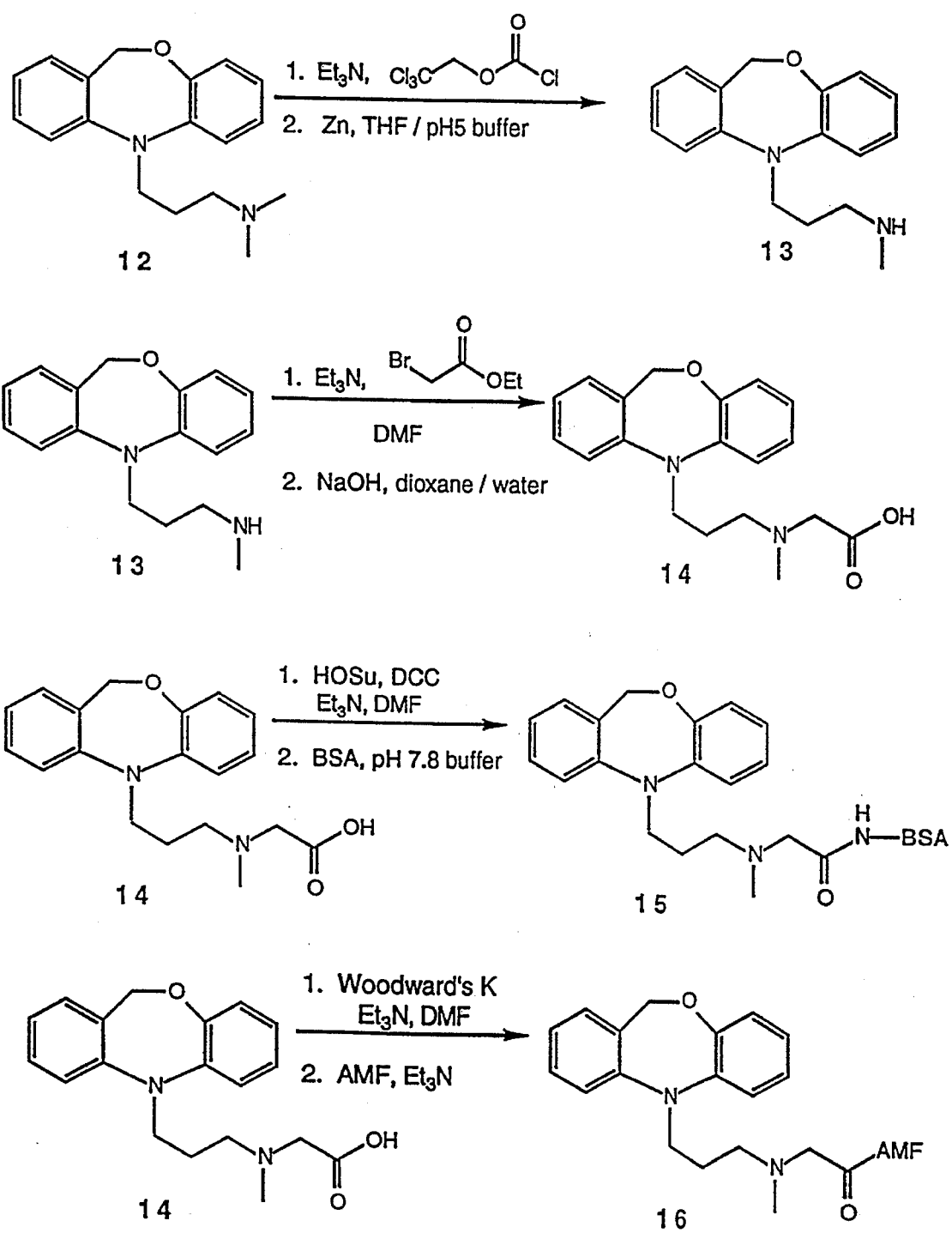
FIG. 3 illustrates the synthetic pathway for the preparation of an immunogen and a fluorescent labeled reagent of the present invention.
Figure 4:
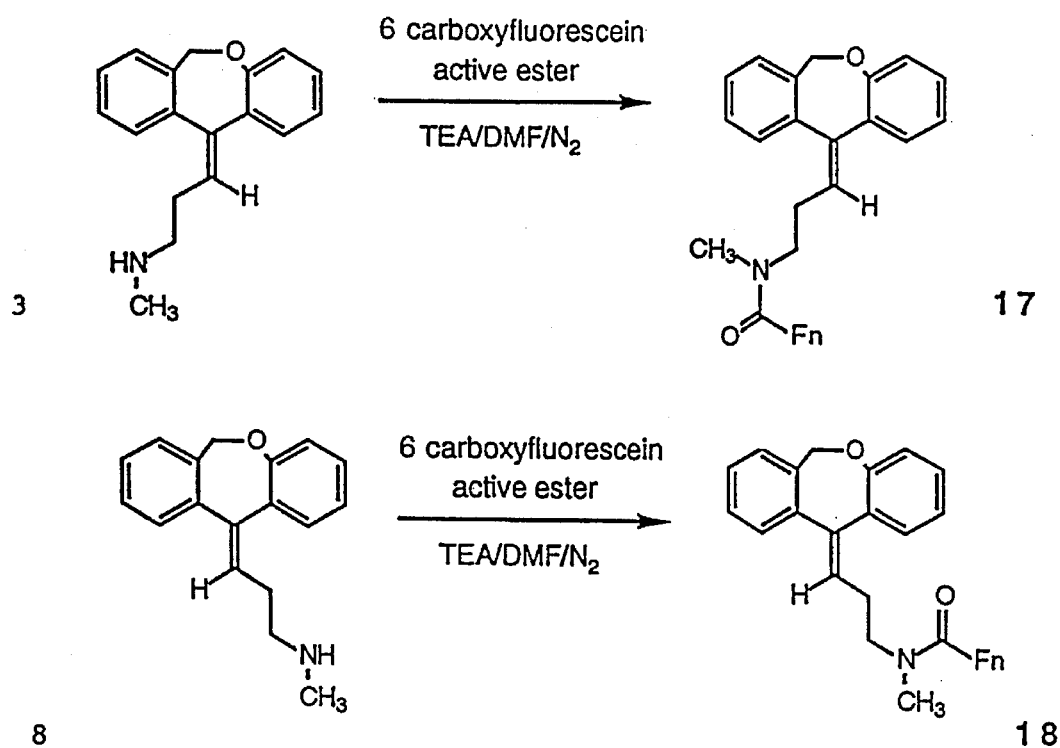
FIG. 4 illustrates the synthetic pathway for the preparation of fluorescent labeled reagents of the present invention.
Figure 4:
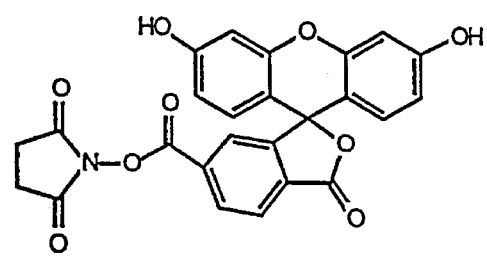
Figure 4:
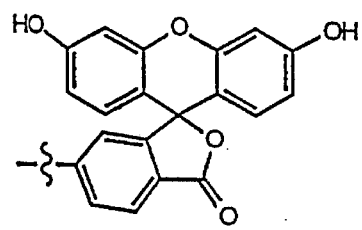
Figure 4:
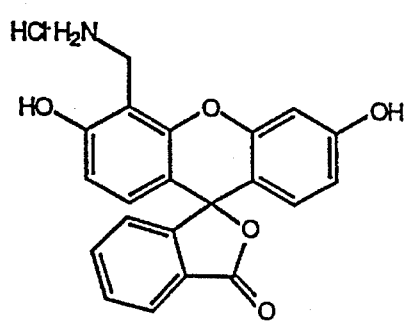
Figure 4:
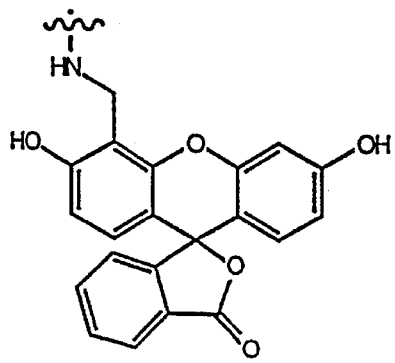

According to the present invention, the quantification of total doxepins is accomplished by first contacting the test sample with a labeled reagent and an antibody reagent, either simultaneously or sequentially in either order, then measuring the amount of the labeled reagent Which either has or has not participated in a binding reaction with the antibody reagent as a function of the amount of total doxepins in the test sample. In particular, the present invention relates to immunogens, antibodies prepared from such immunogens, and labeled reagents for use in the fluorescence polarization immunoassays for the quantification of total doxepins.

According to one embodiment of the present invention, antibodies are produced in one set of a host animal(s) immunized with an E-doxepin immunogen, and antibodies are produced in a separate set of a host animal(s) immunized with a Z-doxepin immunogen, wherein in each of such E and Z immunogens of Formula II, R$_1$ is a linking group comprising from 1 to 6 carbon atoms and 0 to 2 heteroatoms, R$_2$ can be H or CH$_3$, Q is an immunogenic carrier material, and Y-Z is C=CH. The labeled reagent is prepared with the E-doxepin derivative and the Z-doxepin derivative of Formula II, where R$_1$ is a linking group from 1 to 10 carbon and/or heteroatoms, R$_2$ can be H or CH$_3$, and Q is a detectable moiety, and employed as a composition of two such derivatives. The antisera comprises a composition .which is a mixture of each antisera (adjusted to equivalent titer) produced from the E-doxepin immunogen and the Z-doxepin immunogen at a ratio from between 4:1 to 1:4, respectively, preferably from between 2:1 and 1:2, respectively. The labeled reagent comprises a composition of a mixture of the E-doxepin labeled reagent and the Z-doxepin labeled reagent at a ratio of from between 2:1 and 1:6, respectively, preferably from between 1:1 and 1:4, respectively. More preferably, the antisera comprises a composition of a mixture of each antisera (adjusted to equivalent titer) produced from the E-doxepin immunogen and the Z-doxepin immunogen which are present in the composition at a ratio of approximately 1:1, and the labeled reagent comprises a composition of a mixture of the E-doxepin labeled reagent and the Z-doxepin labeled reagent at a ratio of approximately 1:2, respectively.

According to a preferred embodiment of the present invention, immunogens and labeled reagents based on doxepin (where Y-Z is C=CH in Formula II) are employed, in particular, antibodies produced from an E-doxepin immunogen (where $R_2$ is $CH_3$, $R_1$ is carboxymethyl, and Q is bovine serum albumin in Formula II) and a Z-doxepin derivative (where $R_2$ is $CH_3$, $R_1$ is carboxymethyl, and Q is bovine serum albumin in Formula II) are employed in an immunoassay system with a labeled reagent comprising an E-doxepin fluorescent tracer (where $R_2$ is $CH_3$, $R_1$ is C=O, and Q is 6-fluorescein in Formula II) and a Z-doxepin fluorescent tracer (where $R_2$ is $CH_3$, $R_1$ is C=O, and Q is 6-fluorescein in Formula II) is employed. According to this embodiment, the antisera preferably comprises a composition of a mixture of each antisera (adjusted to equivalent titer)-produced from the E-doxepin immunogen and the Z-doxepin immunogen which are present at a ratio of approximately 1:1, and the fluorescent tracer reagent comprises a composition of a mixture of the E-doxepin fluorescent tracer and the Z-doxepin labeled reagent at a ratio of approximately 1:2, respectively. According to another embodiment of the present invention, an immunogen based on dibenzoxazepine (where Y-Z is N-$CH_2$ and $R_2$ is $CH_3$ in Formula II), wherein no isomeric forms thereof exist, and a fluorescent tracer reagent based on doxepin (where Y-Z is C=CH in Formula II) are employed. In particular, antibodies produced from the dibenzoxazepine immunogen (where Y-Z is N-$CH_2$, $R_2$ is $CH_3$, $R_1$ is carboxymethyl, and Q is bovine serum albumin in Formula II) is employed in an immunoassay system with a labeled reagent comprising a fluorescent tracer reagent comprising an E-doxepin tracer (where $R_2$ is $CH_3$, $R_1$ is carboxymethyl, and Q is aminomethyl-fluorescein in Formula II) and a Z-doxepin tracer (where $R_2$ is $CH_3$, $R_1$ is carboxymethyl, and Q is aminomethyl-fluorescein in Formula II) are employed. According to this embodiment, the antisera comprises the antisera produced from the dibenzoxazepine immunogen and the fluorescent tracer reagent comprises a composition of a mixture of the E-doxepin fluorescent tracer and the Z-doxepin fluorescent tracer at a ratio of from between 2:1 and 1:6, preferably from between 1:1 and 1:4, more preferably approximately 1:2, respectively.

Figure 5:
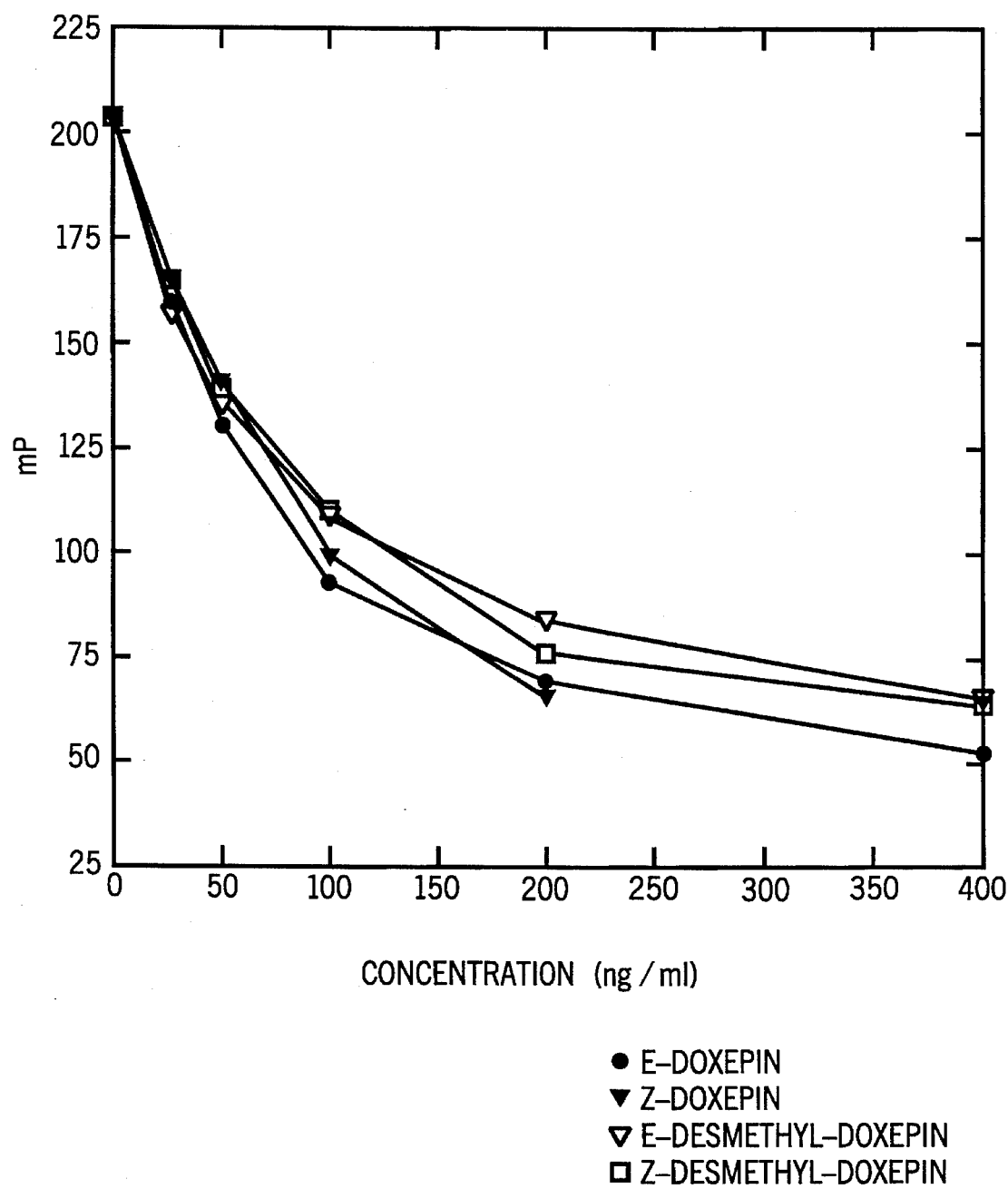
FIG. 5 is a graph which represents the fluorescence polarization immunoassay quantification of doxepin and desmethyldoxepin on an Abbott TDx® Analyzer employing antibodies and labeled reagents prepared from doxepin derivatives which illustrates the change in the mP value obtained for each of the E and Z isomers for doxepin and desmethyldoxepin as determined by the fluorescence polarization immunoassay described in Example 11.
Figure 6:
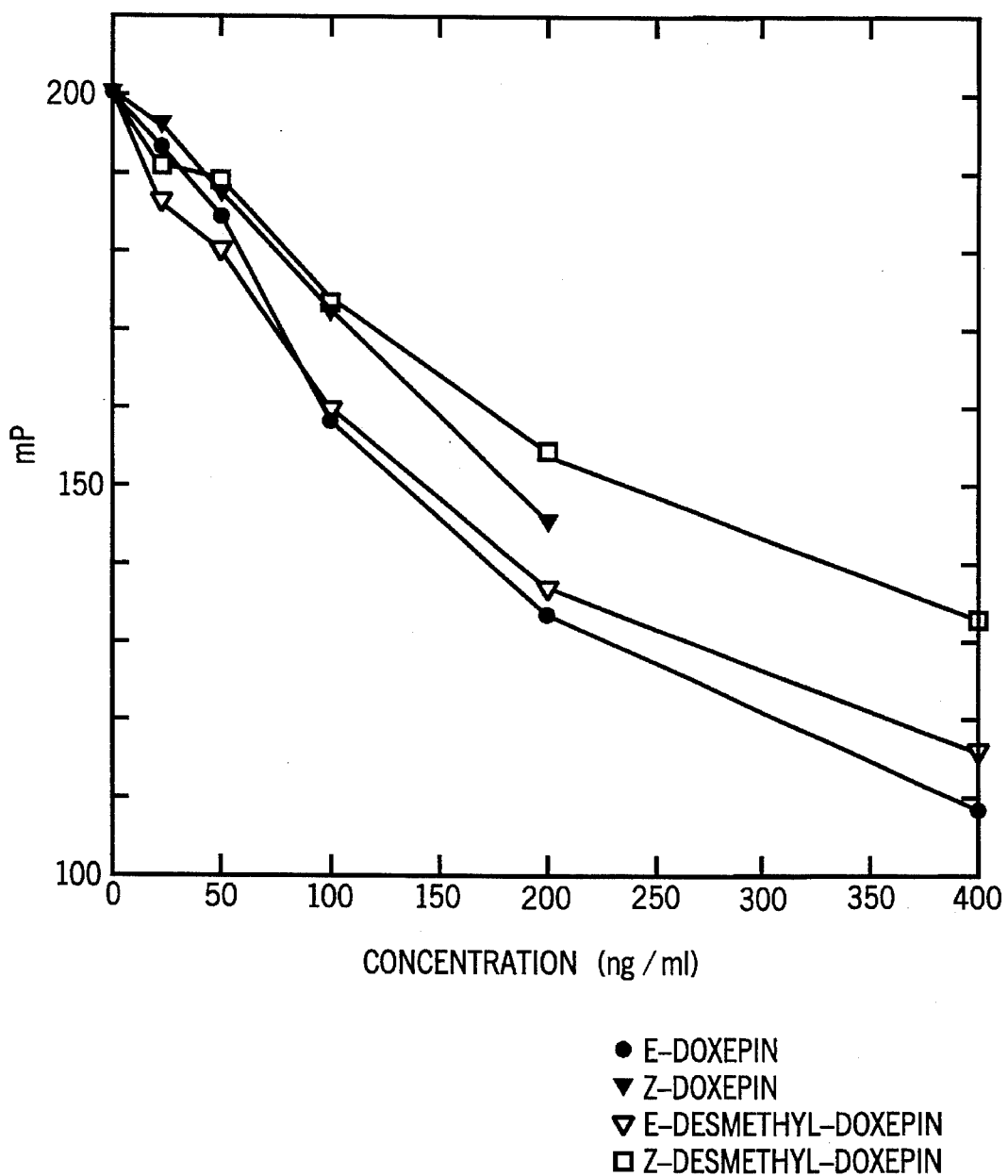
FIG. 6 is a graph which represents the fluorescence polarization immunoassay quantification of total doxepins on an Abbott TDx® Analyzer employing antibodies and labeled reagents prepared from doxepin derivatives which illustrates the change in the mP value obtained for each of the E and Z isomers for doxepin and desmethyldoxepin as determined by the fluorescence polarization immunoassay described in Example 11.

According to the present invention, it was unexpectedly and surprisingly found that for the quantification of total doxepins, the combination of the novel immunogens of Formula II, wherein $R_2$ is $CH_3$, $R_1$ is —$CH_2$—CO—, Y-Z is C=CH and the configuration was E and wherein $R_2$ is $CH_3$, $R_1$ is —$CH_2$—CO—, Y-Z is C=CH and the configuration was Z, and novel fluorescent tracers of Formula II, wherein $R_2$ is $CH_3$, $R_1$ is -CO-, Y-Z is C=CH and the configuration was E and wherein $R_2$ is $CH_3$, $R_1$ is —CO—, Y-Z is C=CH and the configuration was Z was critical for the quantification of total doxepins as intended by the present invention. This advantageous combination of unique reagents offers an advance in the art for the quantification of total doxepins. This composition of isomeric immunogens and isomeric tracers was used to achieve the quantification of total doxepins in test samples which are known to have a wide range of ratios of E-doxepin:(IA, R=$CH_3$):Z-doxepin (IB, R=$CH_3$):E-desdoxepin (IA, R=H):Z-desmethyldoxepin (IB, R=H) as shown in FIG. 5 and FIG. 6. The performance of the above combinations is illustrated by correlation with high-performance liquid chromatography (HPLC) in FIG. 7.

The doxepin derivatives (Formula II) of the present invention can be employed to prepare immunogens by coupling them to conventional carrier materials, and subsequently used to obtain antibodies, or can be used to, form labeled reagents which serve as the detection reagents in immunoassays for determining total doxepins in a test sample. In particular, the doxepin derivatives of the present invention can be coupled to an immunogenic carrier material by various conventional techniques known in the art where, in Formula II, $R_1$ is a linking group comprising from 1 to 6 carbon atoms and 0 to 2 heteroatoms, and Q is an immunogenic carrier material. As would be understood by one skilled in the art, the immunogenic carrier material can be selected from any of those conventionally known and, in most instances, will be a protein or polypeptide, although other materials such as carbohydrates, polysaccharides, ipopolysaccharides, nucleic acids, and the like, of sufficient size and immunogenicity can also be employed. Preferably, the immunogenic carrier material is a protein such as bovine serum albumin, keyhole limpet hemocyanin, thyroglobulin, and the like. The immunogens according to the present invention can be used to prepare antibodies, both polyclonal and monoclonal, according to methods known in the art for use in an immunoassay system according to the present invention. Generally, a host animal, such as a rabbit, goat, mouse, guinea pig, or horse is injected at one or more of a variety of sites with the immunogen, normally in mixture with an adjuvant. Further injections are made at the same site or different sites at regular or irregular intervals thereafter with bleedings being taken to assess antibody titer until it is determined that optimal titer has been reached. The antibodies are obtained by either bleeding the host animal to yield a volume of antiserum, or by somatic cell hybridization techniques or other techniques known in the art to obtain monoclonal antibodies.

When performing an immunoassay for the quantification of total doxepins according to the present invention, various heterogeneous and homogeneous immunoassay system formats known in the art can be followed. Such immunoassay system formats include, but are not intended to be limited to, competitive, sandwich and immunometric techniques. Generally, such immunoassay systems depend upon the ability of an immunoglobulin, i.e., a whole antibody or fragment thereof, to bind to a Specific analyte from a test sample wherein a labeled reagent comprising an antibody of the present invention, or fragment thereof, and a label or detectable moiety is employed to determine the extent of binding. Such detectable labels include, but are not intended to be limited to, enzymes, radiolabels, biotin, toxins, drugs, haptens, DNA, RNA, liposomes, chromophores, chemiluminescers, colored particles and colored microparticles, fluorescent compounds such as aminomethyifluorescein, aminofluorescein, 5-carboxyfluorescein, 6-carboxyfluorescein, 5-fluresceinyl, 6-flouresceinyl, thioureafluorescein, and methoxytriazinolylaminofluorescein, and the like. As described herein, the test sample can be a naturally occurring or artificially formed liquid, or an extract thereof, and includes, but is not intended to be limited to biological test samples such as whole blood, serum, plasma, urine, feces, saliva, cerebrospinal fluid, brain tissue, and the like. In addition, the test sample can be an extract of a test sample, or any derivative thereof.

Typically, the extent of binding in such immunoassay system formats is determined by the amount of the detectable moiety present in the labeled reagent which either has or has not participated in a binding reaction with the analyte, wherein the amount of the detectable moiety detected and measured can be correlated to the amount of analyte present in the test sample. For example, in a competitive immunoassay system, a substance being measured, often referred to as a ligand, competes with a substance of close structural similarity coupled to a detectable moiety, often referred to as a tracer, for a limited number of binding sites on antibodies specific to the portion or portions of the ligand and tracer with structural similarity, shared with an immunogen employed to produce such antibodies.

According to the present invention, the quantification of total doxepins as described herein is particularly useful in a fluorescent polarization immunoassay system wherein the detectable moiety component of the tracer is a fluorescent moiety selected from the group consisting of fluoresceins, aminofluoresceins, aminomethyl-fluoresceins, carboxyfluoresceins, and the like. The amount of tracer bound to the antibody varies inversely to the amount of total doxepins present in the test sample. Accordingly, the relative, and therefore characteristic, binding affinities of total doxepins and the tracer to the antibody binding site, are important parameters of the assay system. Generally, fluorescent polarization techniques are based on the principle that a fluorescent tracer, when excited by plane polarized light of a characteristic wavelength, will emit light at another characteristic wavelength (i.e., fluorescence) that retains a degree of the polarization relative to the incident stimulating light that is inversely related to the rate of rotation of the tracer in a given medium. As a consequence of this property, a tracer substance with constrained rotation, such as in a viscous solution phase or when bound to another solution component with a relatively lower rate of rotation, will retain a relatively greater degree of polarization of emitted light than if in free solution. Therefore, within the time frame in which the ligand and tracer compete for binding to the antibody, the tracer and ligand binding rates should yield an appropriate proportion of free and bound tracer with the preservation of important performance parameters such as selectivity, sensitivity, and precision.

When performing a fluorescent polarization immunoassay for the quantification of total doxepins according to the present invention, a test sample suspected of containing total doxepins is contacted with antiserum prepared with immunogens according to the present invention in the presence of an appropriately selected fluorescein derivative thereof which is capable of producing a detectable fluorescence polarization response to the presence of antiserum prepared with immunogens according to the present invention. Plane polarized light is then passed through the solution to obtain a fluorescence polarization response and the response is detected as a measure of amount of total doxepins present in the test sample.

A test kit according to the present invention comprises all of the essential reagents required to perform a desired fluorescence polarization immunoassay for the total amount of doxepins as described herein. The test kit is presented in a commercially packaged form as a combination of one or more containers holding the necessary reagents, as a composition or admixture where the compatibility of the reagents will allow. Particularly preferred is a test kit for the fluorescent polarization immunoassay quantification of the total amount of doxepins comprising fluorescent tracer compounds and antibodies produced with the immunogens as described above. It is to be understood that the test kit can, of course, include other materials as are known in the art and which may be desirable from a commercial user standpoint, such as buffers, diluents, standards, and the like.

The present invention will now be illustrated, but is not intended to be limited, by the following examples. Numerals which appear in brackets refer to the structural formulae as used in FIGS. 1–4.

EXAMPLE 1

Synthesis Of (E)-Desmethyldoxepin [3]

Solvent abbreviations: $CHCl_3$=chloroform, MeOH=methanol, DMF=dimethylformamide, $CH_2Cl_2$=methylene chloride, $Et_2O$=diethyl ether, EtOAc=ethyl acetate, Hex=hexane, THF=tetrahydrofuran, HOAc=acetic acid.

Doxepin hydrochloride [1](E/Z=85/15) (55.0 g, 0.174 mol) was dissolved in 600 mL $H_2O$, made basic with 6 M NaOH, and extracted with $CHCl_3$ (3×600 mL). The $CHCl_3$ extracts were combined, dried over $Na_2SO_4$, and solvent removed in vacuo. The resulting oil was dissolved in 250 mL EtOH, then 21.15 g (0.182 mol) of maleic acid dissolved in 100 mL EtOH was added slowly, with stirring, followed by an additional 350 mL EtOH. The resulting cloudy solution was refluxed until it became clear, then allowed to stand overnight at room temperature; the resulting crystals were isolated by vacuum filtration. Additional recrystallization from EtOH yielded 41.3 g (0.104 mol) of white crystalline product [2] with an E/Z ratio of 98/2 (determined by HPLC performed on a Waters mporasil column, eluting with EtOAc/MeOH/$NH_4OH$ (90/10/0.2) at a flow rate of 0.7 mL/minute); melting point: 171°–172° C.

(E)-Doxepin maleate [2] (2.50 g, 6.32 mmol) was partially dissolved in 60 mL $H_2O$, made basic with 6 M NaOH, and extracted with $CHCl_3$ (3×60 mL). The $CHCl_3$ extracts were combined, washed with 60 mL brine, dried over $Na_2SO_4$, and solvent removed in vacuo. The resulting oil was redissolved in 10 mL $CHCl_3$, 1.8 mL (13 mmol) of triethylamine added, 1.8 mL (13 mmol) of 2,2,2-trichloroethylchloro-formate added, and reaction stirred under $N_2$ for 3.5 hours. The completed reaction was then diluted with 140 mL $Et_2O$, washed successively with 0.5 M HCl (2×140 mL), $H_2O$ (140 mL), and brine (140 mL), then dried over $MgSO_4$ and solvent removed in vacuo. Resulting material was further purified by silica gel column chromatography, eluting with EtOAc/Hex (20/80), to afford 1.48 g (3.36 mmol) of the desired product as a clear oil; $^1H$ NMR (200 MHz, $CDCl_3$): d 2.5 (q, 2H), 2.8 (d, 3H), 3.5 (t, 2H), 4.6–4.7 (m, 2H), 4.8–5.7 (broad s, 2H), 6.0 (t, 1H), 6.8–6.9 (m, 2H), 7.1–7.4 (m, 6H); mass spec (FAB): (M)+440.

The N-protected (E)-desmethyldoxepin intermediate (1.44 g, 3.27 mmol) was dissolved in 12 mL THF, 2.88 g of zinc powder added, 2.3 mL of 1 M sodium phosphate (pH=5.5) added, and reaction stirred for 17 hours. The reaction mixture was then vacuum filtered, filtrate solvent removed in vacuo, and resulting residue purified by silica gel column chromatography, eluting with THF/MeOH/$NH_4OH$ (85/15/0.4), then THF/MeOH/$NH_4OH$ (75/25/0.4), to afford 744 mg (2.80 mmol) of the desired product [3] as a pale yellow solid; $^1H$ NMR (200 MHz, $CDCl_3$): d 2.5 (s, 3H), 2.7 (m, 2H), 3.0 (m, 2H), 4.7–5.8 (broad s, 2H), 6.0 (t, 1H), 6.8–6.9 (m, 2H), 7.1–7.4 (m, 6H); mass spec (FAB): (M+H)+ 266.

EXAMPLE 2

Synthesis Of Immunogen [5]By Conjugation Of Acid [4] To Bovine Serum Albumin

To a solution of (E)-desmethyldoxepin [3](724 mg, 2.73 mmol) in 10 mL DMF were added, 0.838 mL (6.01 mmol) of triethylamine, 0.605 mL (5.46 mmol) of ethyl bromoacetate, and the reaction was stirred for 17 hours under $N_2$. The completed reaction was then poured into 60 mL H$_2$O, made basic with 6 M NaOH, and extracted with Et$_2$O (3×60 mL). The ether extracts were combined washed with 60 mL brine, dried over MgSO$_4$, and solvent removed in vacuo. Crude product was purified by silica gel column chromatography, eluting with EtOAc/Hex (50/50), to afford 511 mg (1.45 mmol) of the desired product as a clear oil; $^1$H NMR (200 MHz, CDCl$_3$): d 1.2 (t, 3H), 2.3 (s, 3H), 2.4 (m, 2H), 2.6 (t, 2H), 3.2 (s, 2H), 4.2 (q, 2H), 4.7–5.8 (broad s, 2H), 6.0 (t, 1H), 6.8–6.9 (m, 2H), 7.1–7.4 (m, 6H); mass spec (DCI-NH$_3$): (M+H)+352.

The intermediate ester (460 mg, 1.31 mmol) was dissolved in 8.4 mL MeOH, 4.2 mL of 10% NaOH added, and solution stirred for 30 minutes. The reaction mixture was then diluted with 30 mL H$_2$O, pH adjusted to 3–4 with 1 M HCl, and extracted with CHCl$_3$ (3×35 mL). The CHCl$_3$ extracts were combined, washed with 35 mL brine, dried over Na$_2$SO$_4$, and solvent removed in vacuo to yield 424 mg (1.31 mmol) of the desired product [4]as a white solid; $^1$H NMR (200 MHz, CDCl$_3$): d 2.5–2.7 (m, 2H), 2.6 (s, 3H), 3.2 (m, 2H), 3.4 (s, 2H), 4.7–5.8 (broad s, 2H), 6.0 (t, 1H), 6.5 (broad s, 2H), 6.8–6.9 (m, H), 7.1–7.4 (m, 6H); mass spec (DCI-NH$_3$): (M+H)+324.

The free acid [4](59 mg, 0.18 mmol) was dissolved in 0.86 mL DMF, 25 mg (0.22 mmol) of N-hydroxysuccinimide added, 45 mg (0.22 mmol) of 1,3-dicyclohexylcarbodiimide added, and reaction stirred for 17 hours under N$_2$. The reaction was then filtered into a solution consisting of 306 mg of bovine serum albumin (BSA) dissolved in 5.35 mL of 0.1 M sodium phosphate (pH=7.8) and 1.4 mL DMF. This reaction was stirred overnight, then dialyzed against 2 L of 0.1 M sodium phosphate (pH=7.8) for 2 hours, then against H$_2$O .(8× 2 L). After lyophilization, 276 mg of the desired immunogen [5]was obtained as a fluffy white solid.

EXAMPLE 3

Synthesis Of Tracer [6]By Conjugation Of Acid [4]To Aminomethylfluorescein

The free acid [4](11 mg, 0.034 mmol) was dissolved in 0.50 mL DMF, 9 mg (0.04 mmol) of 2-ethyl-5-phenylisoxazolium-3'-sulfonate (Woodward's K) added, pH adjusted to 9 with triethylamine, and reaction stirred under N$_2$ for 40 minutes. Then 14 mg (0.034 mmol) of aminomethylfluorescein hydrochloride was added, reaction pH again adjusted to 9 with triethylamine, and solution stirred under N$_2$, in the dark, for 16 hours. Solvent was then removed in vacuo and the crude residue purified on a single 1 mm preparative C18 chromatography plate, eluting with H$_2$O/MeOH/HOAc (20/80/0.4), to yield 9 mg (0.01 mmol) of the desired product [6]as an orange solid; mass spec (FAB): (M+H)+667.

EXAMPLE 4

Synthesis Of (Z)-Desmethyldoxepin [8]

Doxepin hydrochloride [1](E/Z=85/15) (100 g, 0.317 mol) was dissolved in 800 mL H$_2$O, made basic with 6 M NaOH, and extracted with CHCl$_3$ (3×800 mL). The CHCl$_3$ extracts were combined, dried over Na$_2$SO$_4$, and solvent removed in vacuo. The resulting oil was dissolved in 700 mL EtOH, then 36.7 g (0.317 mol) of maleic acid dissolved in 600 mL EtOH was added slowly, with stirring. The resulting cloudy solution was refluxed until clear, then allowed to stand overnight at room temperature. Crystals were isolated by vacuum filtration and the mother liquor saved. Crystals were recrystallized two additional times as above, and the three mother liquors saved and combined and solvent removed in vacuo. Recrystallization of mother liquor material from refluxing EtOH eventually afforded 24 g of a mother liquor product which was 65% Z isomer in composition (determined by HPLC performed on a Waters m porasil column, eluting with EtOAc/MeOH/NH$_4$OH (90/10/0.2) at a flow rate of 0.7 mL/minute). Recrystallization of this material from 450 mL EtOH gave crystals (9.1 g) which were 80% Z isomer. This material was recrystallized from 170 mL CHCl$_3$/CCl$_4$ (50/50) at 4° C., yielding 7.65 g of crystalline material which was 87% Z isomer in composition. Three additional recrystallizations from CHCl$_3$/CCl$_4$ eventually afforded 5.12 g (12.9 mmol) of the desired product [7]with an E/Z ratio of 4/96; melting point: 162°–163° C.

(Z)-Doxepin maleate [7](1.00 g, 2.53 mmol) was partially dissolved in 35 mL H$_2$O, made basic with 6 M NaOH, and extracted with CHCl$_3$ (3×35 mL). The CHCl$_3$ extracts were combined, washed with 35 mL brine, dried over Na$_2$SO$_4$, and solvent removed in vacuo. The resulting oil was redissolved in 4 mL CHCl$_3$, 0.65 mL (4.7 mmol) of triethylamine added, 0.65 mL (4.7 mmol) of 2,2,2-trichloroethyl-chloroformate added, and reaction stirred under N$_2$ for 3.5 hours. The completed reaction was then diluted with 50 mL Et$_2$O, washed successively with 0.5 M HCl (2×50 mL), H$_2$O (50 mL), and brine (50 mL), then dried over MgSO$_4$ and solvent removed in vacuo. Resulting material was further purified by silica gel column chromatography, eluting with EtOAc/Hex (20/80), to afford 710 mg (1.61 mmol) of the desired product as a clear oil; $^1$H NMR (200 MHz, CDCl$_3$): d 2.7 (q, 2H), 2.9 (d, 3H), 3.5 (t, 2H), 4.6–4.7 (m, 2H), 5.0–5.4 (broad s, 2H), 5.7 (t, 1H), 6.9 (m, 2H), 7.1–7.4 (m, 6H); mass spec (FAB): (M)+440.

The N-protected (Z)-desmethyldoxepin (679 mg, 1.54 mmol) was dissolved in 5.7 mL THF, 1.36 g of zinc powder added, 1.1 mL of 1 M sodium phosphate (pH=5.5) added, and reaction stirred for 17 hours. The reaction mixture was then vacuum filtered, filtrate solvent removed in vacuo, and resulting residue purified by silica gel column chromatography, eluting with THF/MeOH/NH$_4$OH (85/15/0.4), then THF/MeOH/NH$_4$OH (82/18/0.4), to afford 364 mg (1.37 mmol) of the desired product [8]as a pale yellow solid; $^1$H NMR (200 MHz, CD30D): d 2.7 (s, 3H), 2.8 (q, 2H), 3.2 (t, 2H), 5.1–5.3 (broad s, 2H), 5.7 (t, 1H), 6.8–7.0 (m, 2H), 7.1–7.4 (m, 6H); mass spec (DCI-NH$_3$): (M+H)+266.

EXAMPLE 5

Synthesis Of Immunogen [10]By Conjugation Of Acid [9] To Bovine Serum Albumin (Z)-Desmethyldoxepin [8](336 mg, 1.27 mmol) was stirred in 4 mL DMF, 0.39 mL (2.8 mmol) of triethylamine added, 0.28 mL (2.5 mmol) of ethyl bromoacetate added, and reaction stirred for 17 hours under N$_2$. The completed reaction was then poured into 30 mL H20, made basic with 6 M NaOH, and extracted with Et20 (3×30 mL). The ether extracts were combined washed with 30 mL brine, dried over MgSO$_4$, and solvent removed in vacuo. Crude product was purified by silica gel column chromatography, eluting with EtOAc/Hex (50/50), to afford 191 mg (0.543 mmol) of the desired product as a yellow oil; $^1$H NMR (200 MHz, CDCl$_3$): d 1.2 (t, H), 2.4 (s, 3H), 2.5–2.8 (m, 4H), 3.2 (s, 2H), 4.2 (q, 2H), 5.1– 5.3 (broad s, 2H), 5.7 (t, 1H), 6.8–7.0 (m, 2H), 7.1–7.4 (m, 6H); mass spec (DCI-NH$_3$): (M+H)+ 352.

The intermediate ester ( 180 mg, 0.51 mmol) was dissolved in 3.3 mL MeOH, 1.64 mL of 10% NaOH added, and solution stirred for 30 minutes. The reaction mixture was then diluted with 10 mL H$_2$O, pH adjusted to 3–4 with 1 M HCl, and extracted with CHCl$_3$ (3×10 mL). The CHCl$_3$ extracts were combined, washed with 10 mL brine, dried over Na$_2$SO$_4$, and solvent removed in vacuo to yield 166 mg (0.51 mmol) of the desired product [9] as a white foam; $^1$H NMR (200 MHz, CDCl$_3$): d 2.7 (s, 3H), 2.7–2.9 (m, 2H), 3.2–3.4 (m, 2H), 3.5 (s, 2H), 5.1–5.3 (broad s, 2H), 5.7 (t, 1H), 5.9–6.3 (broad s, 2H), 6.8–7.0 (m, 2H), 7.1–7.4 (m, 6H); mass spec (DCI-NH$_3$): (M+H)+ 324.

The free acid [9](65 mg, 0.20 mmol) was dissolved in 0.94 mL DMF, 28 mg (0.24 mmol) of N-hydroxysuccinimide added, 50 mg (0.24 mmol) of 1,3-dicyclohexylcarbodiimide added, and reaction stirred for 17 hours under N$_2$. The reaction mixture was then filtered into a solution consisting of 342 mg of bovine serum albumin dissolved in 5.8 mL of 0.1 M sodium phosphate (pH =7.8) and 1.5 mL DMF. This reaction was stirred overnight, then dialyzed against 2 L of 0.1 M sodium phosphate (pH =7.8) for 3 hours, then against H$_2$0 (7× 2 L). After lyophilization, 317 mg of the desired immunogen [10]was obtained as a fluffy white solid.

EXAMPLE 6

Synthesis Of Tracer [11]By Conjugation Of Acid [9]To Aminomethylfluorescein

The acid [9](12 mg, 0.037 mmol) was dissolved in 0.50 mL DMF, 10 mg (0.041 mmol) of 2-ethyl-5-phenylisoxazolium-3'-sulfonate added, pH adjusted to 9 with triethylamine, and reaction stirred under N$_2$ for 40 minutes. Then 15 mg (0.037 mmol) of aminomethylfluoroescein hydrochloride was added, reaction pH again adjusted to 9 with triethylamine, and solution stirred under N$_2$, in the dark, for 16 hours. Solvent was then removed in vacuo and the crude residue purified on a single 1 mm preparative C18 chromatography plate, eluting with H$_2$0/MeOH/HOAc (10/90/0.4), to yield 17 mg (0.025 mmol) of the desired product [11]as an orange solid; mass spec (FAB): (M+H)+667.

EXAMPLE 7

Synthesis Of N$^I$-(3-Methylaminopropyl)-Dibenz[b,f]-[1,4]-Oxazepine [13]

Trichloroethyl chloroformate (0.90 mL, 6.53 mmol) was added dropwise to a 0° C. solution of N$^1$-(3-dimethylaminopropyl)-dibenz[b,f]-[1,4]-oxazepine [12](580 mg, 2.05 mmol), triethylamine (Et$_3$N) (1.02 mL, 7.18 mmol) and 6 mL chloroform under nitrogen and stirred 10 minutes at 0° C. then 16 hours at room temperature. The reaction mixture was poured into 30 mL water, pH was adjusted to 13 with 2N NaOH, separated layers, extracted with 3×25 mL ethyl acetate (EtOAc), combined all organic layers and dried over potassium carbonate. Removal of the solvents in vacuo gave an orange oil which was purified by column chromatography (150 g silica gel; 20% THF / 79% hexane/1% Et$_3$N; v/v) to obtain 545 mg (60%) of the desired intermediate carbamate. $^1$H HMR (200 MHz, CDCl$_3$)d 7.4–7.3 (m, 3H), 7.1–6.9 (m, 3H), 6.9–6.8 (m, 2H), 5.3 (s, 2H), 4.6 (d, 2H), 3.8 (t, 2H), 3.4 (t, 2H), 2.9 (s, 3H), 1.9 (p, 2H); mass spec (DCI, NH$_3$) (M+H)+443.

Zinc powder (2.40 g, 36.6 mmol) was added to a solution containing the N-protected intermediate (540 mg, 1.22 mmol) in 20 mL THF/3 mL 1.0 M KH$_2$PO$_4$ (pH 4.4) buffer and stirred 12.5 hours at room temperature. The reaction was filtered and the solid was washed with 3×20 mL EtOAc and 1×5 mL 1 N HCl; the filtrate was adjusted to pH 12 with 2N NaOH, layers separated, extracted filtrate with 2×30 mL EtOAc, combined organic layers and dried over potassium carbonate. The solvents were removed in vacuo to give a yellow oil which was purified by column chromatography (100 g silica gel; 15% MeOH/84% CH$_2$Cl$_2$/1% Et$_3$N; v/v) to afford 62 mg (80%) of the desired secondary amine [13]N$^1$-(3-methyl-aminopropyl)-di-benz[b,f]-[1,4] -oxazepine. $^1$H NMR (200 MHz, CDCl$_3$)d 7.3–7.2 (m, 2H), 7.1–6.9 (m, 3H), 6.9–6.7 (m, 3H), 5.3 (s, 2H), 3.8 (t, 2H), 2.6 (t, 2H), 2.4 (s, 3H), 2.2 (s, 1H), 1.8 (p, 2H); mass spec (DCI, NH$_3$) (M+H)+269.

EXAMPLE 8

Synthesis Of Immunogen [15]

Bromoethyl acetate (0.22 mL, 1.95 mmol) was added to a solution of triethylamine (Et$_3$N) (0.63 mL, 4.5 mmol), N$^I$-(3-methylamino-propyl)-dibenz-[b,f]-[ 1,4]-oxazepine [13] (260 mg, 0.97 mmol) and 7 mL dimethylformamide (DMF) under nitrogen and stirred for 19 hours at room temperature. The reaction mixture was poured into 100 mL water, pH was adjusted to 13 with 2N NaOH, extracted with 3×75 mL diethyl ether, combined organic layers and dried over potassium carbonate. The solvents were removed in vacuo to give a yellow oil which was purified by column chromatography (75 g silica gel; 15% methanol/85% methylene chloride/0.5% Et$_3$N; v/v) to afford 330 mg (96%) of the desired intermediate amino ester. $^1$H NMR (200 MHz, CDCl$_3$) d 7.4–7.2 (m, 2H), 7.2–6.9 (m, 3H), 6.9–6.7 (m, 3H), 5.3 (s, 2H), 4.1 (q, 2H), 3.8 (t, 2H), 3.2 (s, 2H), 2.5 (t, 2H), 2.3 (s, 3H), 1.8 (p, 2H), 1.3 (t, 3H); mass spec (FAB) (M+H)+355.

An aqueous solution of sodium hydroxide (2.8 mL, 2.ON NaOH, 5.6 mmol) was added to a solution of the desired intermediate amino ester (245 mg, 0.69 mmol)/5 mL dioxane, 2 mL distilled water and stirred for one hour at room temperature. The reaction was poured into 30 mL water, adjusted pH to 13 with 2N NaOH, extracted 1×25 mL toluene, adjusted to pH 4 with 1N HCl, extracted 3×25 mL chloroform and combined chloroform extracts. The solvents were removed in vacuo to afford 65 mg (28%) of the desired acid 14]as an off-white solid. $^1$H NMR (200 MHz, CDCl$_3$:CD$_3$0D, 1) d 7.7 (s, 1H), 7.4–7.3 (m, 2H), 7.1–7.0 (m, 3H), 6.9–6.7 (m, H), 5.3 (s, 2H), 3.9 (t, 2H), 3.5 (s, 2H), 3.2 (t, 2H), 2.7 (s, 3H), 2.0 (p, 2H); mass spec (FAB) (M+H)+327.

A flask was charged with the following: dicyclohexylcarbodiimide (DCC) (44.8 mg, 0.217 mmol), N-hydroxysuccinimide (24.7 mg, 0.215 mmol), acid [14](64 mg, 0.195 mmol) and 1.5 mL dimethylformamide (DMF); stirred 21 hours under nitrogen at room temperature and filtered to afford a clear solution of the desired active ester. This solution was added to a 17° C. solution of bovine serum albumin (BSA) (207 mg, 0.00305 mmol) in 5 mLpH 7.8, 0.1 M phosphate buffer/1.5 mL DMF and stirred overnight. The reaction mixture was dialyzed in the following order: 1×2L pH 7.8, 0.1 M phosphate buffer, 5×2L distilled water and lyophilized the remaining contents of the dialysis bag to afford 202 mg of the desired immunogen, [15].

EXAMPLE 9

Synthesis Of Tracer[16]

Triethylamine (0.020 mL, 0.14 mmol) was added to a solution of acid [14](15 mg, 0.046 mmol)/Woodward's K (12.9 mg, 0.051 mmol)/0.9 mL DMF under nitrogen and stirred 1 hour whereupon amino-methylfluorescein (19.2 mg, 0.048 mmol) and triethylamine (0.03 mL, 0.21 mmol) were added to the reaction mixture. The solution was stirred 2 days, solvents removed in vacuo and resulting orange solid purified to afford 15 mg of the desired tracer [16]. Mass Spec: (FAB) (M+H)+672.

EXAMPLE 10

Synthesis Of Tracers [17]and [18]

6-Carboxyfluorescein (500 mg, 1.33 mmol) was dissolved in 7 mL DMF, 184 .mg (1.59 mmol) of N-hydroxysuccinimide was added, 328 mg (1.59 mmol) of 1,3dicyclohexylcarbodiimide was added, and reaction stirred for 17 hours, under $N_2$, in the dark. The reaction mixture was then vacuum filtered, filtrate combined with 353 mg (1.33 mmol) of (E)-desmethyldoxepin [3], 0.28 mL (2.0 mmol) of triethylamine added, and solution stirred under $N_2$, in the dark, for 24 hours. Reaction solvent was then removed in vacuo, and crude oil purified by silica gel chromatography, eluting with $CH_2Cl_2$/MeOH (90/10), then $CH_2Cl_2$/MeOH (70/30), to afford 544 mg (0.872 mmol) of the desired product [17]as an orange solid; mass spec (FAB): (M+H)+624.

6-Carboxyfluorescein (762 mg, 2.02 mmol) was dissolved in 8 mL DMF, 280 mg (2.43 mmol) of N-hydroxysuccinimide was added, 501 mg (2.43 mmol) of 1,3dicyclohexylcarbodiimide was added, and reaction stirred for 17 hours under $N_2$, in the dark. The reaction was then vacuum filtered, filtrate combined with 538 mg (2.03 mmol) of (Z)-desmethyldoxepin [8], 0.57 mL (4.1 mmol) of triethylamine added, and solution stirred under $N_2$ in the dark, for 24 hours. Reaction solvent was then removed in vacuo, and crude oil purified by silica gel chromatography, eluting with $CH_2Cl_2$/MeOH (90/10), then $CH_2Cl_2$/MeOH (70/30), to afford 281 mg (0.451 mmol) of the desired product [18]as an orange solid; mass spec (FAB): (M+H)+624.

EXAMPLE 11

Fluorescent Polarization Immunoassay For Total Doxepins (a) Antisera was prepared from 6 rabbits immunized with the E-doxepin immunogen [5]and 6 rabbits immunized with the Z-doxepin immunogen [10]as described in Examples 2 and 5. Individual titers indicated that the average titer of each group of 6 rabbits was approximately equivalent. The raw antisera was mixed at a volume ratio of 1:1 and diluted with a buffer containing 109 mM phosphate buffer, 50 mM disodium EDTA, 0.01% bovine gamma-globulin, and 0.105% sodium azide (pH =6.65).

The fluorescent tracer (Example 10) was formulated by preparing the E-doxepin tracer [17]at 82 nM and the Z-doxepin tracer [18]at 82 nM, both in a buffer containing 50 mM ACES, 150 mM NaCl, 0.1% sodium azide, and 25% DMF (pH 6.8). The two solutions were then mixed at a volume ratio of 1:2 (E:Z), giving final concentrations of approximately 27 nM and 55 nM for the E and Z isomers, respectively.

Prior to analysis, each test sample was pretreated as described in pending patent application U.S. Ser. No. 627,282, filed Dec. 14, 1990. To a polypropylene tube was added a test sample (0.25 mL), 0.9 mL of heptane/isoamyl alcohol (35:1 v/v), and 0.1 mL of a 25% sodium carbonate solution. The mixture was vortexed vigorously for one minute and then centrifuged at 9,500×g for 30 seconds. To another polypropylene tube was added 0.5 mL of the upper layer from the first tube, 0.1 mL of 0.05 N HCl, and 0.04 mL of chloramine T (0.04 mg/mL water). The mixture was vortexed for 30 seconds, let stand for 2 minutes, and centrifuged at 9,500×g for 30 seconds. Finally, 0.085 mL of the lower phase from the second tube was transferred to an Abbott TDx® Therapeutic Drug Monitoring System Analyzer (Abbott Laboratories, Abbott Park, Ill. USA) sample cartridge.

The assay was run according to the standard TDx protocol on a TDx analyzer in which the sample (0.02 mL) was contacted with 0.025 mL of antisera and 0.025 mL of tracer in a total buffer volume of 2 mL. Results are expressed by millipolarization (mP) units.

Standard curves were prepared using a calibrator formulated to contain 42.5% E-doxepin, 7.5% Z-doxepin, 25% E-desmethyldoxepin, and 25% Z-desmethyldoxepin (on a molar ratio) in a buffer containing 50 mM phosphate buffer, 150 mM NaCl, 0.1% sodium azide, and 0.07% bovine serum albumin (pH 6.5). Each of the analytes was compared individually to this standard curve as shown in FIG. 5.

(b) Antisera was prepared from 6 rabbits immunized with the dibenzoxazepine immunogen [15]as described in Example 8. The raw antisera was diluted with a buffer containing 109 mM phosphate buffer, 50 mM disodium EDTA, 0.01% bovine gamma-globulin, and 0.105% sodium azide (pH=6.65).

The fluorescent tracer was formulated by preparing the E-doxepin tracer ([6], Example 3) at 82 nM and the Z-doxepin tracer ([11], Example 6) at 82 nM, both in a buffer containing 50 mM ACES, 150 mM NaCl, 0.1% sodium azide, and 5% DMF (pH=6.8). The two solutions were then mixed at a volume ratio of 1:2 (E:Z), giving final concentrations of approximately 27 nM and 55 nM for the E and Z isomers, respectively.

Prior to analysis, each test sample was pretreated as described in paragraph (a). To a polypropylene tube was added a test sample (0.25 mL), 0.9 mL of heptane/isoamyl alcohol (35:1 v/v), and 0.1 mL of a 25% sodium carbonate solution. The mixture was vortexed vigorously for one minute and then centrifuged at 9,500×g for 30 seconds. To another polypropylene .tube was added 0.5 mL of the upper layer from the first tube, 0.1 mL of 0.05 N HCl, and 0.04 mL of chloramine T (0.04 mg/mL water). The mixture was vortexed for 30 seconds, let stand for 2 minutes, and centrifuged at 9,500×g for 30 seconds. Finally 0.085 mL of the lower phase from the second tube was transferred to the TDx sample cartridge.

The assay was run according to the standard TDx protocol on a TDx analyzer in which the sample (0.02 mL) was contacted with 0.025 mL of antisera and 0.025 mL of tracer in a total buffer volume of 2 mL. Results are expressed by millipolarization (mP) units.

Standard curves were prepared using a calibrator formulated to contain 42.5% E-doxepin, 7.5% Z-doxepin, 25% E-desmethyl-doxepin, and 25% Z-desmethyldoxepin (on a molar ratio) in a buffer containing 50 mM phosphate buffer, 150 mM NaCl, 0.1% sodium azide, and 0.07% bovine serum albumin (pH 6.5). Each of the analytes was compared individually to this standard curve as shown in FIG. 6.

EXAMPLE 14

COMPARATIVE ANALYSIS OF TOTAL DOXEPINS TDx ASSAY VS. HPLC

The relative accuracy of the Total Doxepins TDx assay was determined by correlation with HPLC using patient sample extracts. The extracts for HPLC analysis were prepared as described below and the tricyclic antidepressants loxapine and amoxapine were used, each at a concentration of 4 m g/mL in acetonitrile, as internal standards.

1. Pipette 1.0 mL of patient standard into a 16×125 silylated tube fitted with a teflon screw cap. Remove the appropriate standard calibration curve frozen aliquots from the freezer and allow to thaw. Add 0.75 mL of acetonitrile containing the internal standard to each tube.
2. Add 1.0 mL of 0.25 N NaOH followed by 0.200 mL of isoamyl alcohol, vortex vigorously, and allow the tubes to stand for 5.0 min.
3. Into each tube pipette 10.0 mL of n-heptane and tightly secure the cap of each tube. Shake the heptane/plasma biphasic mixture vigorously for 1.0 hour.
4. Remove the tubes from the shaker and transfer to the centrifuge. Centrifuge the heptane/plasma mixtures for min at at least 2000×gravity(g) to clarify the layer.
5. Remove the tubes from the centrifuge and transfer the heptane upper layer to another silylated tube of the same description containing 1.0 mL of 0.1 M, pH 3 glycylglycine buffer. Cap these tubes and shake vigorously for 1.0 hour.
6. Remove the tubes from the shaker and transfer to a centrifuge. Centrifuge the biphasic glycyl-glycine/heptane mixture for 30 min. at at least 2000×g.
7. Remove the tubes from the centrifuge, uncap and aspirate or pipette off the heptane upper layer and discard it.
8. Add 2.0 mL of 0.25 N NaOH to each remaining glycylglycine lower phase. Add 5.0 mL of n-pentane to each aqueous extract, cap the tubes and shake for 1.0 hour.
9. Remove the tubes from the shaker and transfer to a centrifuge. Centrifuge the pentane/aqueous mixture at 200× g for 30 min.
10. Remove the tubes from the centrifuge and transfer the pentane upper layer to a 16×100 silylated conical screw top test tube. Place the caps on the test tubes tightly and unscrew ¼ turn. Place the tubes in a warm sand bath, transfer the sand bath containing the tubes to a vacuum desicator cabinet and apply the vacuum. Approximately 25–30 min is required for the pentane to evaporate.
11. Remove the tubes in the sand bath from the desicator and pipette into each tube 1.0 mL of pentane, recap and vortex each tube briefly. Open the caps ¼ turn and return the tubes to the desicator and reapply the vacuum for 10–15 min. until the pentane has evaporated.
12. Remove the dry tubes from the desicator and pipette in 0.070 mL of HPLC mobile phase. Vortex each tube for approx. 30 sec taking care to wet the tube sides.
13. Transfer the tubes to a centrifuge and centrifuge at 200×g for 2–3 min.
14. Remove the tubes from the centrifuge and transfer the entire contents to the WISP autocarousel sample cuvettes. The injection volume is set at 0.050 mL per injection onto a 10 cm.×0.6 cm. column packed with 3 micron silica with an 80 Angstrom pore size. The chromatographic mobile phase consisted of a mixture of 80 parts 0.025 M dibasic sodium phosphate adjusted to pH 3 with concentrated phosphoric acid/20 parts acetonitrile/0.021 M n-nonylamine(pH range= 7.4–7.8). The analytical column is equipped with a dry packed guard column containing 40 micron pellicular silica. The solvent flow rate was 1.6 mL/min.

Figure 7:
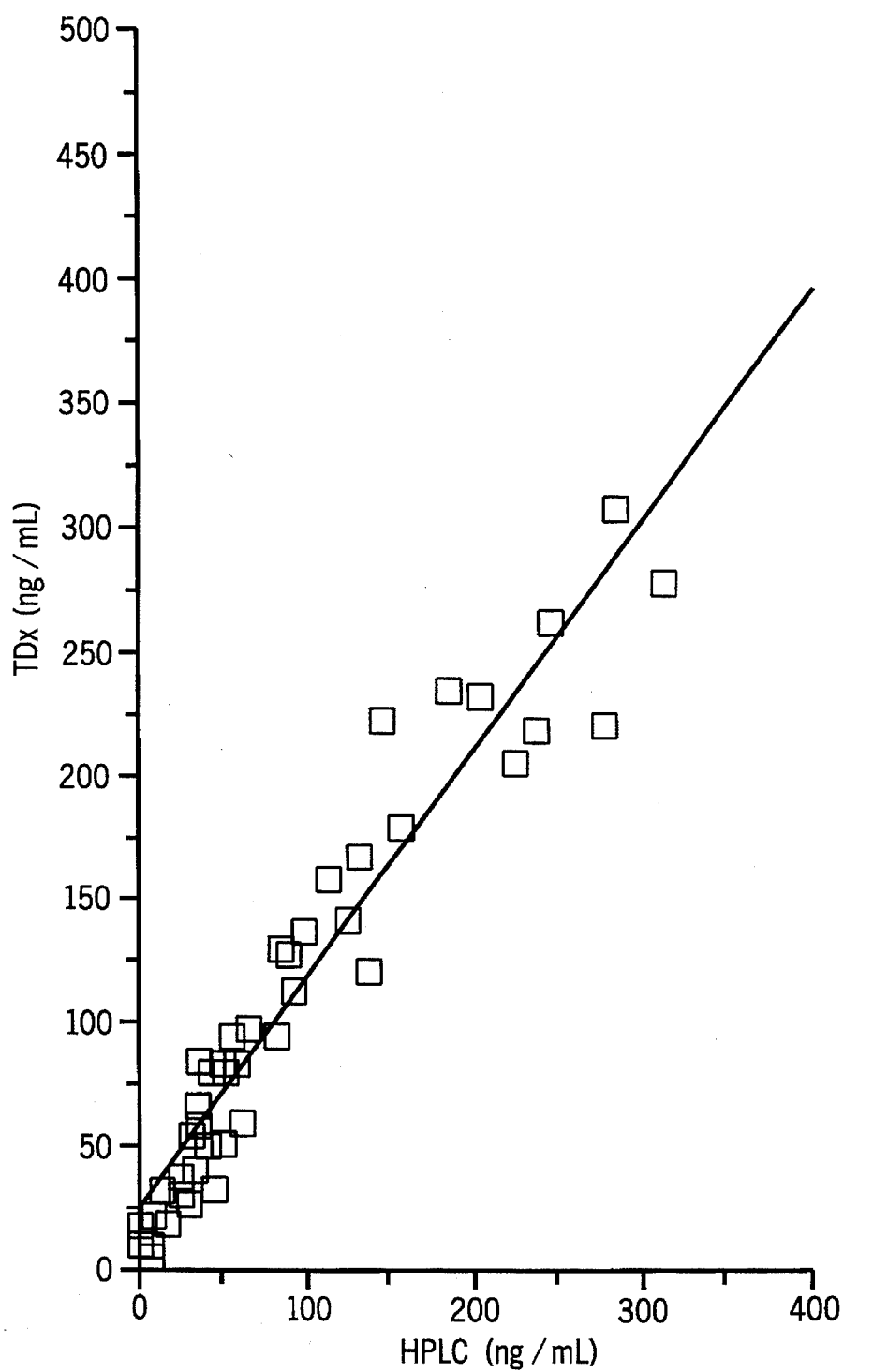
FIG. 7 is a graph which illustrates the accuracy of the method of fluorescence polarization immunoassay on an Abbott TDx® Analyzer, as described in Example 11 for the quantification of total doxepins of the present invention compared to high performance liquid chromatography.

Linear regression analysis showed good correlation between the Total Doxepins TDx Assay and the HPLC assay (N=103, R=0.9612, S=0.93667). The results are shown in FIG. 7.

It will be apparent that many modifications and variations of the present invention as herein set forth are possible without departing from the spirit and scope hereof, and that, accordingly, such limitations are imposed only as indicated by the appended claims.

We claim:

1. A labeled reagent which is recognizable by antibodies capable of binding total doxepins in a test sample, said total doxepins comprising one or more of E-doxepin, Z-doxepin, E-desmethyl-doxepin, and Z-desmethyldoxepin, wherein said labeled reagent is a doxepin derivative of the formula:

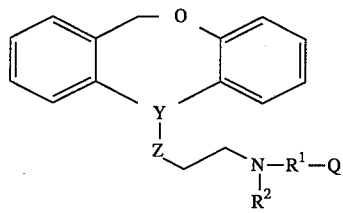

where Y-Z is C=CH or N-CH$_2$, R$_1$ is a linking group comprising from 1 to 6 carbon atoms and 0 to 2 heteroatoms, R$_2$ can be H or CH$_3$, and Q is a detectable moiety, wherein said labeled reagent comprises a composition of the E-isomer and the Z-isomer; of said doxepin derivative.

2. The labeled reagent of claim 1 wherein said detectable moiety is selected from the group consisting of enzymes, chromophores, fluorescent molecules, chemiluminescent molecules, phosphorescent molecules, and luminescent molecules.

3. The labeled reagent of claim 1 wherein said detectable moiety is a fluorescent molecule which is selected from the group consisting of aminomethylfluorescein, aminofluorescein, 5-carboxyfluorescein, 6-carboxyfluorescein, thioureafluorescein, and methoxytriazinolyl-aminofluorescein.

4. The labeled reagent of claim 1 wherein Y-Z is C=CH wherein said labeled reagent comprises a composition of the E-isomer of said labeled reagent and the Z-isomer of said labeled reagent, said mixture having a ratio of from between about 2:1 (E:Z) and 1:6 (E:Z).

5. The labeled reagent of claim 4 wherein said labeled reagent composition ratio is from between 1:1 and 1:4.

6. The labeled reagent of claim 4 wherein said labeled reagent composition ratio is 1:1.

7. The labeled reagent of claim 1 wherein Y-Z is N-CH$_2$.

8. A compound of the formula:

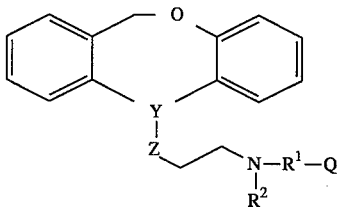

wherein Y-Z is the E-isomer of C=CH, the Z-isomer of C=CH or N-CH$_2$, R$_1$ is a linking group comprising from 1 to 6 carbon atoms and 0 to ,2 heteroatoms, R$_2$ can be H or CH$_3$, and Q is a detectable moiety or an immunogenic carrier material.

9. A compound of claim 8 where Y-Z is the E isomer of C=CH, $R_2$ is $CH_3$, $R_1$ is —$CH_2$—CO— and Q is aminomethylfluorescein.

10. A compound of claim 8 where Y-Z is the Z isomer of C=CH, $R_2$ is $CH_3$, $R_1$ is —$CH_2$—CO— and Q is aminomethylfluorescein.

11. A compound of claim 8 where Y-Z is the E isomer of C=CH, $R_2$ is H, $R_1$ is —$CH_2$—CO— and Q is aminomethylfluorescein.

12. A compound of claim 8 where Y-Z is the Z isomer of C=CH, $R_2$ is H, $R_1$ is —$CH_2$—CO— and Q is aminomethylfluorescein.

13. A compound of claim 8 where Y-Z is N-$CH_2$, $R_2$ is $CH_3$, $R_1$ is —$CH_2$—CO— and Q is aminomethylfluorescein.

14. A compound of claim 8 where Y-Z is N-$CH_2$, $R_1$ is H, $R_2$ is —$CH_2$—CO— and Q is aminomethylfluorescein.

15. A compound of claim 8 where Y-Z is the E isomer of C=CH, $R_2$ is $CH_3$, $R_1$ is —$CH_2$—CO— and Q is bovine serum albumin.

16. A compound of claim 8 where Y-Z is the Z isomer of C=CH, $R_2$ is $CH_3$, $R_1$ is —$CH_2$—CO— and Q is bovine serum albumin.

17. A compound of claim 8 where Y-Z is the E isomer of C=CH, $R_2$ is H, $R_1$ is —$CH_2$—CO— and Q is bovine serum albumin.

18. A compound of claim 8 where Y-Z is the Z isomer of C=CH, $R_2$ is H, $R_1$ is —$CH_2$—CO— and Q is bovine serum albumin.

19. A compound of claim 8 where Y-Z is N-$CH_2$, $R_2$ is $CH_3$, $R_1$ is —$CH_2$—CO— and Q is bovine serum albumin.

* * * * *

UNITED STATES PATENT AND TRADEMARK OFFICE
CERTIFICATE OF CORRECTION

PATENT NO. : 5,464,767
DATED : November 7, 1995
INVENTOR(S) : M. Adamczyk, J.R. Fishpaugh, R.E. Hruska, D. Johnson It is certified that error appears in the above-indentified patent and that said Letters Patent is hereby corrected as shown below:

Column 1, line 26, change "subthera, peutic" to

--subtherapeutic--.

Column 2, line 34, change "clic:" to

--clic--.

Column 3, line 25, change "desmethyidoxepins" to

--desmethyldoxepins--.

Column 4, line 33, change "Which" to

--which--.

Column 4, line 55, change ".which" to

--which--.

Column 5, line 6, change "employed, in" to

--employed. In--.

Column 6, line 3, change "to," to

--to--.

Column 6, line 16, change "ipopolysaccharides" to

--lipopolysaccharides--.

UNITED STATES PATENT AND TRADEMARK OFFICE
CERTIFICATE OF CORRECTION

PATENT NO. : 5,464,767
DATED : November 7, 1995
INVENTOR(S) : M. Adamczyk, J.R. Fishpaugh, R.E. Hruska, D. Johnson Page 2 of 4

It is certified that error appears in the above-indentified patent and that said Letters Patent is hereby corrected as shown below:

Column 6, line 43, change "Specific" to

--specific--.

Column 6, line 51, change "aminomethyifluorescein" to

--aminomethylfluorescein--.

Column 8, line 58, change "(M+H)+" to

--(M+H)+--.

Column 9, line 11, change "(M+H)+352" to

--(M+H)+352--.

Column 9, line 23, change "(M+H)+324" to

--(M+H)+324--.

Column 9, line 33, change ".(8 x 2L)." to

--(8 x 2L).--.

Column 9, line 51, change "+667" to

--+667--.

Column 10, line 43, change "CD3OD" to

--$CD_3OD$--.

UNITED STATES PATENT AND TRADEMARK OFFICE
CERTIFICATE OF CORRECTION

PATENT NO. : 5,464,767
DATED : November 7, 1995
INVENTOR(S) : M. Adamczyk, J.R. Fishpaugh, R.E. Hruska, D. Johnson It is certified that error appears in the above-indentified patent and that said Letters Patent is hereby corrected as shown below:

Column 10, line 56, change "H20" to

--$H_2O$--.

Column 10, line 57, change "Et20" to

--$Et_2O$--.

Column 10, line 63, change "(t, H)" to

--(t, 3H)--.

Column 12, line 9, change "62" to

--262--.

Column 12, line 43, change "14]" to

--[14]--.

Column 12, line 44, change "1)" to

--4:I)--.

Column 12, line 45, change "(m, H)" to

--(m, 3H)--.

UNITED STATES PATENT AND TRADEMARK OFFICE
CERTIFICATE OF CORRECTION

PATENT NO. : 5,464,767
DATED : November 7, 1995
INVENTOR(S) : M. Adamczyk, J.R. Fishpaugh, R.E. Hruska, D. Johnson It is certified that error appears in the above-indentified patent and that said Letters Patent is hereby corrected as shown below:

Column 14, line 31, change "5%" to --25%--.

Column 15, line 17, in front of "min" insert --30--.

Column 16, line 65, change ",2" to --2--.

Column 16, line 65, change "can be" to --is--.

Signed and Sealed this

Twenty-second Day of October, 1996

Attest:

BRUCE LEHMAN

Attesting Officer   Commissioner of Patents and Trademarks